(12) United States Patent
Podhajsky et al.

(10) Patent No.: US 10,888,368 B2
(45) Date of Patent: Jan. 12, 2021

(54) ELECTROSURGICAL DISSECTOR WITH THERMAL MANAGEMENT

(71) Applicant: COVIDIEN LP, Mansfield, MA (US)

(72) Inventors: Ronald J. Podhajsky, Boulder, CO (US); Kristel L. Ambrosius, Cary, NC (US)

(73) Assignee: COVIDIEN LP, Mansfield, MA (US)

( * ) Notice: Subject to any disclaimer, the term of this patent is extended or adjusted under 35 U.S.C. 154(b) by 16 days.

(21) Appl. No.: 16/273,286

(22) Filed: Feb. 12, 2019

(65) Prior Publication Data

US 2019/0167337 A1 Jun. 6, 2019

Related U.S. Application Data

(62) Division of application No. 15/679,398, filed on Aug. 17, 2017, now Pat. No. 10,206,732, which is a (Continued)

(51) Int. Cl.
*A61B 18/14* (2006.01)
*A61B 18/08* (2006.01)
(Continued)

(52) U.S. Cl.
CPC .......... *A61B 18/082* (2013.01); *A61B 18/085* (2013.01); *A61B 18/1445* (2013.01);
(Continued)

(58) Field of Classification Search
CPC ....... A61B 18/082; A61B 18/08; A61B 18/12; A61B 18/14; A61B 18/1402; A61B 18/1477; A61B 2018/126; A61B 2018/1467; A61B 2018/1497; A61B 2018/162; A61B 2018/165; A61B 2018/00595; A61B 2018/00607;
(Continued)

(56) References Cited

U.S. PATENT DOCUMENTS 4,862,890 A 9/1989 Stasz et al.
5,403,312 A 4/1995 Yates et al.
(Continued)

FOREIGN PATENT DOCUMENTS

CN 101069652 A 11/2007
CN 203354640 U 12/2013

OTHER PUBLICATIONS

European Search Report dated Oct. 2, 2013 from counterpart European Application No. EP13171636.7. (10 pgs.).
(Continued)

*Primary Examiner* — Thomas A Giuliani

(57) ABSTRACT

An electrosurgical dissection apparatus is disclosed, and includes a thermally insulating body, a thermally conductive insert, at least one active electrode, and at least one return electrode. The at least one active electrode is disposed on the thermally conductive insert, and the at least one return electrode is spaced from the at least one active electrode by a portion of the thermally insulating body. The thermally conductive insert is configured to cauterize tissue dissected by radiofrequency energy passing from the at least one active electrode to the at least one return electrode.

14 Claims, 9 Drawing Sheets

Related U.S. Application Data division of application No. 13/898,601, filed on May 21, 2013, now Pat. No. 9,757,181.

(60) Provisional application No. 61/658,523, filed on Jun. 12, 2012.

(51) Int. Cl.
*A61B 18/18* (2006.01)
*A61B 18/00* (2006.01)
*A61B 18/16* (2006.01)

(52) U.S. Cl.
CPC .......... *A61B 18/1477* (2013.01); *A61B 18/18* (2013.01); *A61B 2018/0063* (2013.01); *A61B 2018/00095* (2013.01); *A61B 2018/00101* (2013.01); *A61B 2018/00107* (2013.01); *A61B 2018/00148* (2013.01); *A61B 2018/00595* (2013.01); *A61B 2018/00994* (2013.01); *A61B 2018/1427* (2013.01); *A61B 2018/1467* (2013.01); *A61B 2018/1497* (2013.01); *A61B 2018/162* (2013.01); *A61B 2018/165* (2013.01)

(58) Field of Classification Search
CPC .......... A61B 2018/00589; A61B 2018/00601; A61B 2018/00994; A61B 2018/0063; A61B 2018/00095; A61B 2018/00101
USPC ............... 606/37, 39, 40, 41, 45, 48, 49, 50; 607/98, 99, 113, 115, 116
See application file for complete search history.

(56) References Cited

U.S. PATENT DOCUMENTS

| | | | |
|---|---|---|---|
| 5,688,270 A | 11/1997 | Yates et al. | |
| 5,925,039 A | 7/1999 | Landingham | |
| 6,241,723 B1 | 6/2001 | Heim et al. | |
| 6,287,305 B1 | 9/2001 | Heim et al. | |
| 6,575,968 B1* | 6/2003 | Eggers | A61B 18/148 606/41 |
| 6,582,429 B2 | 6/2003 | Krishnan et al. | |
| 6,770,072 B1 | 8/2004 | Truckai et al. | |
| 6,859,239 B2 | 2/2005 | DeLong | |
| 6,905,497 B2 | 6/2005 | Truckai et al. | |
| 7,011,657 B2 | 3/2006 | Truckai et al. | |
| 7,041,102 B2 | 5/2006 | Truckai et al. | |
| 7,083,619 B2 | 8/2006 | Truckai et al. | |
| 7,087,054 B2 | 8/2006 | Truckai et al. | |
| 7,112,201 B2 | 9/2006 | Truckai et al. | |
| 7,147,638 B2 | 12/2006 | Chapman et al. | |
| 7,156,846 B2 | 1/2007 | Dycus et al. | |
| 7,160,298 B2 | 1/2007 | Lawes et al. | |
| 7,277,770 B2 | 10/2007 | Huang | |
| 7,377,919 B2 | 5/2008 | Heim et al. | |
| 8,421,583 B2* | 4/2013 | Koyama | H01C 7/028 338/13 |
| 9,757,181 B2 | 9/2017 | Podhajsky et al. | |
| 10,206,732 B2 | 2/2019 | Podhajsky et al. | |
| 2001/0001314 A1 | 5/2001 | Davison et al. | |
| 2002/0111622 A1 | 8/2002 | Khandkar et al. | |
| 2003/0014044 A1 | 1/2003 | Krishnan et al. | |
| 2003/0078577 A1* | 4/2003 | Truckai | A61B 18/1442 606/51 |
| 2003/0216732 A1 | 11/2003 | Truckai et al. | |
| 2003/0220637 A1 | 11/2003 | Truckai et al. | |
| 2004/0215185 A1* | 10/2004 | Truckai | A61B 18/1442 606/41 |
| 2005/0159745 A1 | 7/2005 | Truckai et al. | |
| 2006/0089638 A1 | 4/2006 | Carmel et al. | |
| 2006/0178667 A1 | 8/2006 | Sartor et al. | |
| 2006/0217706 A1 | 9/2006 | Lau et al. | |
| 2006/0264929 A1 | 11/2006 | Goble et al. | |
| 2008/0195093 A1 | 8/2008 | Couture et al. | |
| 2008/0249595 A1 | 10/2008 | McDaniel | |
| 2009/0047445 A1 | 2/2009 | Schneider et al. | |
| 2009/0062794 A1 | 3/2009 | Buysse et al. | |
| 2010/0204560 A1 | 8/2010 | Salahieh et al. | |

OTHER PUBLICATIONS

Chinese First Office Action for CN 201310229301.7 dated Jun. 3, 2016.

Chinese Second Office Action for Chinese Appln. No. CN 201310229301.7 dated Feb. 27, 2017.

* cited by examiner

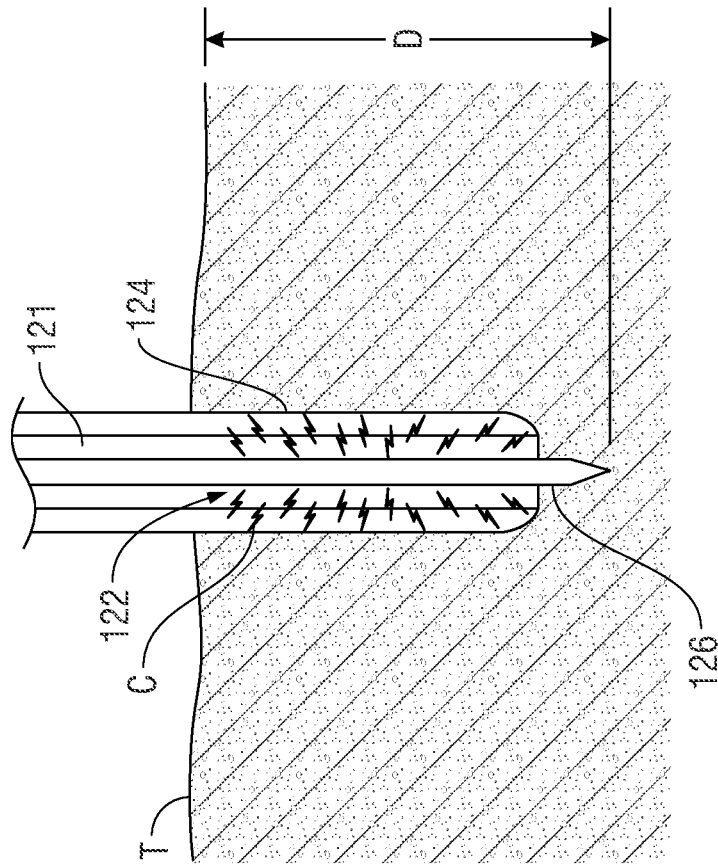
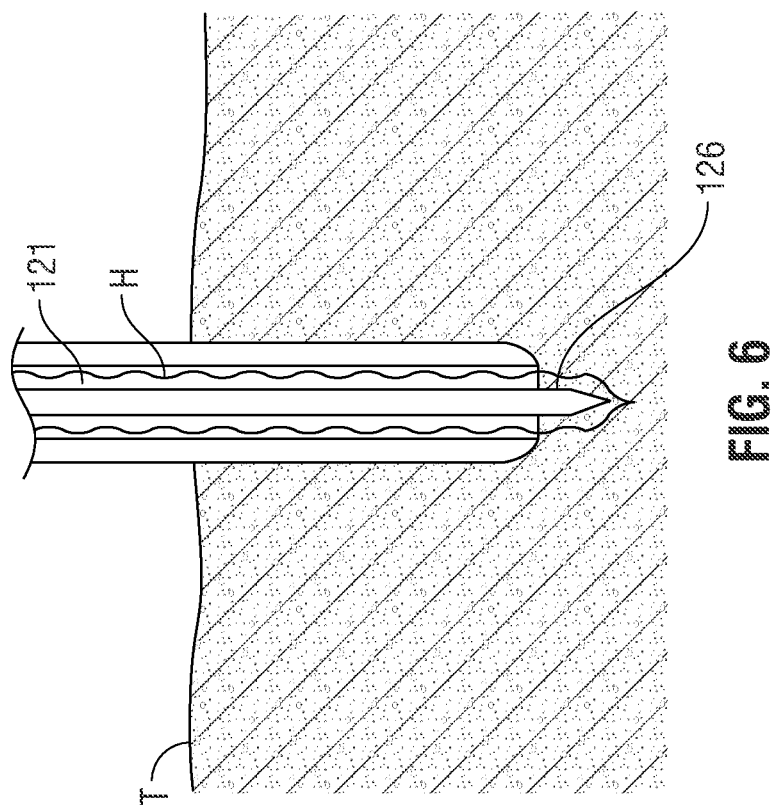

ELECTROSURGICAL DISSECTOR WITH THERMAL MANAGEMENT

CROSS REFERENCE TO RELATED APPLICATION

The present patent application is a divisional of U.S. patent application Ser. No. 15/679,398, filed Aug. 17, 2017, now U.S. Pat. No. 10,206,732, which is a divisional of U.S. patent application Ser. No. 13/898,601, filed May 21, 2013, now U.S. Pat. No. 9,757,181, which claims the benefit of and priority to U.S. Provisional Patent Application Ser. No. 61/658,523, filed on Jun. 12, 2012. The entire contents of each of the foregoing applications are hereby incorporated herein by reference.

BACKGROUND

Technical Field

The present disclosure relates to an electrosurgical dissection system and method for performing electrosurgical dissection procedures. More particularly, the present disclosure relates to a system and method for transmitting radio frequency energy from an electrosurgical generator to a treatment site through a dissector formed of materials having thermal profiles allowing for the selective storage and deposit of thermal energy into surrounding tissue.

Background of Related Art

Electrosurgery involves application of high radio frequency electrical current to a surgical site to cut, ablate, or cauterize tissue, or to coagulate blood. In monopolar electrosurgery, a source or active electrode delivers radio frequency energy from the electrosurgical generator to the tissue and a return electrode carries the current back to the generator. In this configuration, the active electrode is typically part of a surgical instrument held by the surgeon and applied to the tissue to be treated. A patient return electrode is placed remotely from the active electrode to carry the current back to the generator.

In bipolar electrosurgery, one of the electrodes of a hand-held instrument functions as the active electrode and the other as the return electrode. The return electrode is placed in close proximity to the active electrode such that an electrical circuit is formed between the two electrodes (e.g., electrosurgical forceps or electrosurgical pencils). In this manner, the applied electrical current is limited to the body tissue positioned between the electrodes. When the electrodes are sufficiently separated from one another, the electrical circuit is open and thus inadvertent contact of body tissue with either of the separated electrodes prevents current flow.

Since electrosurgical procedures generate thermal energy through the active electrode, the absorption and storage of thermal energy by the electrosurgical pencil body is of particular importance. When the active electrode is not receiving power or is between cycles in AC power generation, thermal energy stored in the electrosurgical pencil body is transmitted to surrounding tissue. It is desirable to provide an electrosurgical pencil having a body with a thermal profile that provides for the controlled and directed release of thermal energy into surrounding tissue.

SUMMARY

As used herein, the term "distal" refers to that portion that is further from an operator while the term "proximal" refers to that portion that is closer to an operator. The term "dissection" may refer to cutting, ablating, or cauterizing tissue, and may additionally refer to the resultant coagulation of blood therefrom.

As used herein the term "electrosurgical pencil" is intended to include instruments which have a handpiece which is attached to an active electrode and which is used to dissect tissue. Typically, the electrosurgical pencil may be operated by a handswitch or a foot switch. The "active electrode" is an electrically conducting element which is usually elongated and may be in the form of a thin flat blade with a pointed or rounded distal end.

As used herein, the terms "energy" and "electrosurgical energy" refers broadly to include all types of energy used to treat tissue, e.g., RF energy, ultrasonic energy, microwave energy, thermal energy, light energy, etc.

According to one aspect of the present disclosure, an electrosurgical dissection apparatus is disclosed, and includes a thermally insulating body, a thermally conductive insert, at least one active electrode, and at least one return electrode. The at least one active electrode is disposed on the thermally conductive insert, and the at least one return electrode is spaced from the at least one active electrode by a portion of the thermally insulating body. The thermally conductive insert is configured to cauterize tissue dissected by radiofrequency energy passing from the at least one active electrode to the at least one return electrode.

In one aspect of the present disclosure, the at least one active electrode may be formed from copper, silver, or gold. In another aspect of the present disclosure, the at least one active electrode may be formed from a coating of conductive material such as copper, silver, or gold.

In another aspect of the present disclosure, the thermally insulating body may be formed from an amorphous polyamide. In one aspect of the present disclosure, the thermally conductive insert may be formed from alumina.

In a further aspect of the present disclosure, the electrosurgical dissection apparatus further includes at least a pair of approximatable jaw members each including a sealing plate. Each of the at least one active electrode and the at least one return electrode may be disposed on a respective opposing sealing plate.

According to another aspect of the present disclosure, an electrosurgical dissection system is disclosed, and includes an electrosurgical generator and an electrosurgical dissection apparatus. The electrosurgical dissection apparatus includes a thermally insulating body, a thermally conductive insert, at least one active electrode, and at least one return electrode. The at least one active electrode is disposed on the thermally conductive insert, and the at least one return electrode is spaced from the at least one active electrode by a portion of the thermally insulating body. The thermally conductive insert is configured to cauterize tissue dissected by radiofrequency energy passing from the at least one active electrode to the at least one return electrode. In another aspect of the present disclosure, the at least one active electrode is electrically coupled with the electrosurgical generator.

In one aspect of the present disclosure, an electrosurgical dissection apparatus comprises a body defining a longitudinal axis and includes a plurality of electrodes, a thermally insulating portion, and a thermally conductive portion proximal of the thermally insulating portion. The thermally conductive portion is configured to store thermal energy generated by at least one electrode of the plurality of electrodes for release into tissue.

In another aspect of the present disclosure, the body may have a tapered profile. In yet another aspect of the present disclosure, at least one electrode of the plurality of electrodes may be coated with an electrically conductive material. In another aspect of the present disclosure, the thermally conductive portion of the body may be formed of alumina. In still another aspect of the present disclosure, the thermally insulating portion may be formed of an amorphous polyamide.

In another aspect of the present disclosure, a method of using an electrosurgical apparatus having an active electrode, a return electrode, and an electrically insulating section is disclosed. The method includes supplying current between the active electrode and the return electrode such that tissue is dissected. The method also includes cauterizing tissue with thermal energy stored in the electrically insulating section.

BRIEF DESCRIPTION OF THE DRAWINGS

Various aspects of the present disclosure are described herein with reference to the drawings wherein:

FIG. 5 is a top partial view of the active electrosurgical pencil shown in FIG. 4, inserted into a layer of tissue;

FIG. 6 is a top partial view of the electrosurgical pencil as shown in FIG. 5, with the electrodes inactive and a thermally conductive insert radiating thermal energy to the surrounding tissue;

DETAILED DESCRIPTION

Particular embodiments of the present disclosure are described hereinbelow with reference to the accompanying drawings. In the following description, well-known functions or constructions are not described in detail to avoid obscuring the present disclosure in unnecessary detail. Those skilled in the art will understand that the invention according to the present disclosure may be configured for use with either monopolar or bipolar electrosurgical systems and either an endoscopic instrument or an open instrument. It should also be appreciated that different electrical and mechanical connections and other considerations apply to each particular type of instrument.

Figure 1:
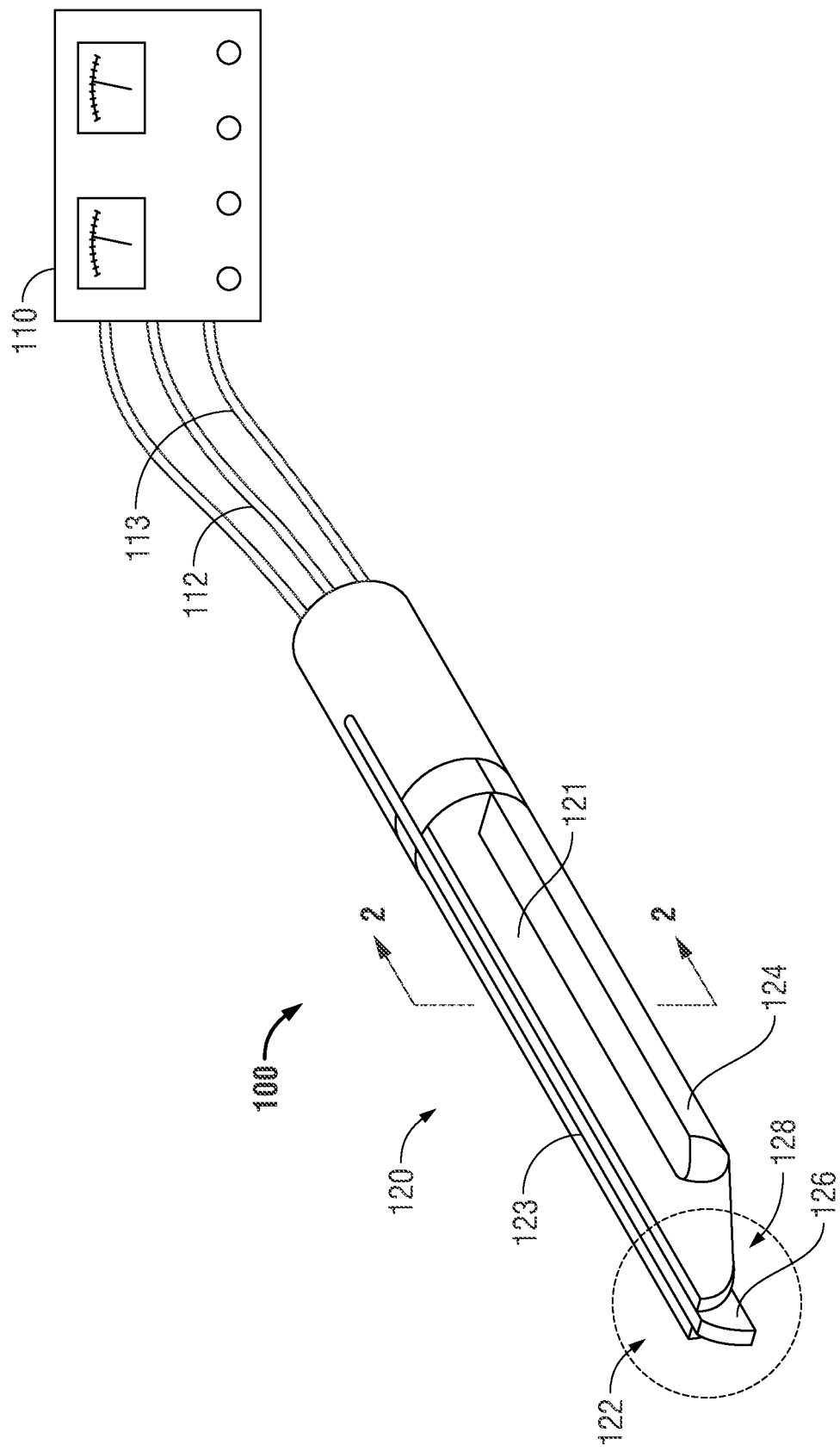
FIG. 1 is a perspective view of the presently disclosed electrosurgical dissection system including an electrosurgical pencil coupled to an electrosurgical generator.

FIG. 1 is a perspective view of an electrosurgical dissection system 100. The electrosurgical system 100 includes an electrosurgical generator 110 that supplies electrosurgical radio frequency ("RF") energy to a bipolar electrosurgical pencil 120 via one or more coaxial cables 112 or transmission wires 113. Electrosurgical generator 110 may include a number of user controls for varying the amplitude and wavelength of the energy supplied to electrosurgical pencil 120. Electrosurgical dissection system 100 and the intercooperating relationships of the various components are explained in greater detail in U.S. Publication No. 2006/0178667, the entire contents of which are hereby incorporated by reference.

Figure 4:
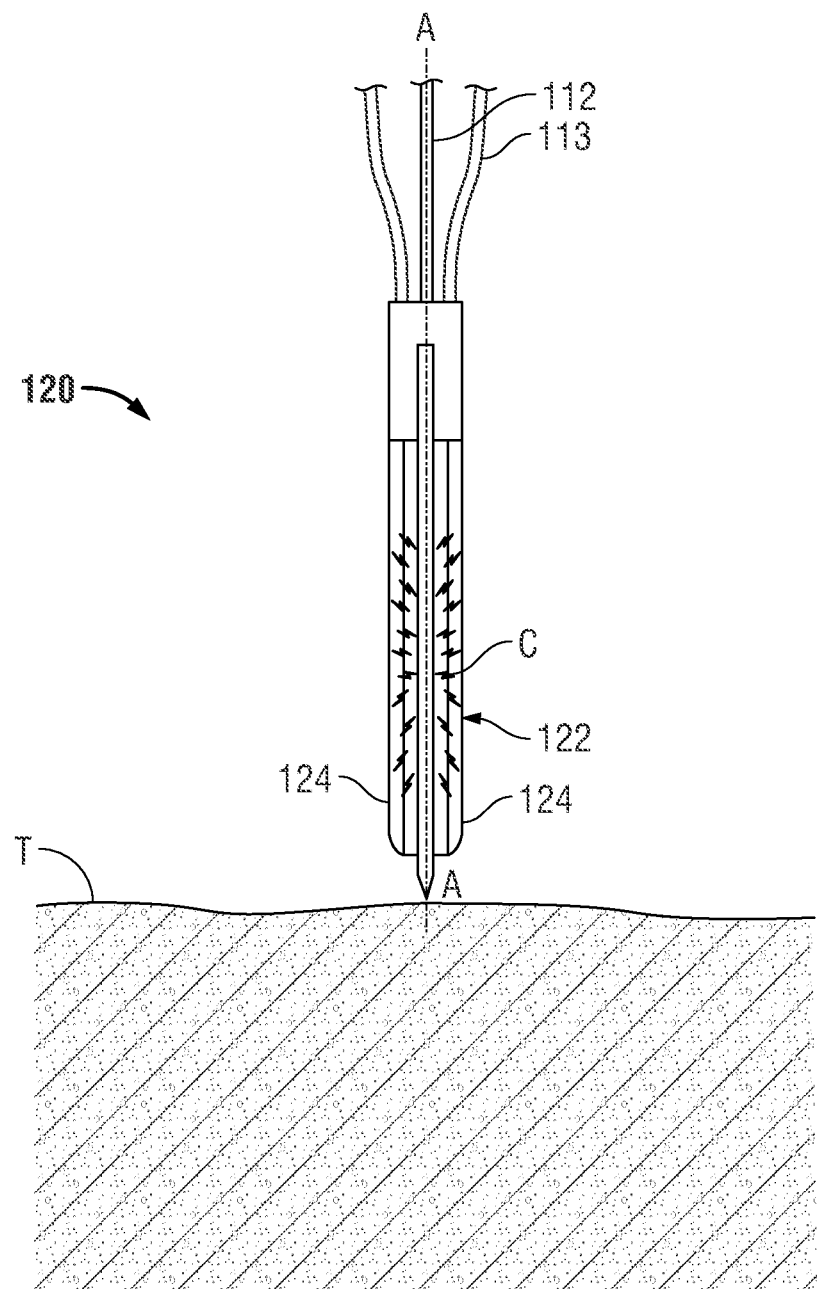
FIG. 4 is a top view of the electrosurgical pencil with electrical current flowing from the active electrode to the return electrodes, and prior to insertion into tissue.

Electrosurgical pencil 120 is configured for dissecting body tissue "T" (FIG. 4). Electrosurgical pencil 120 has an elongate body 121 defining a longitudinal axis "A" (FIG. 4) that narrows toward distal tip 128. The body 121 of electrosurgical pencil 120 may be thin and blade-like, or may have any other desirable configuration. Distal tip 128 may be pointed, rounded, or blunt, and includes a portion of an active electrode 122 formed of an electrically conductive material such as copper, silver, or gold. The formation of active electrode 122 will be described in further detail below. Active electrode 122 is electrically coupled to electrosurgical generator 110 through one or more coaxial cables 112. Additional transmission wires 113 may be power cables or leads suitable for electrical coupling of electrosurgical generator 110 and electrosurgical pencil 120. Electrosurgical pencil 120 may include a handle portion suitable for engagement by an operator, such as a pistol grip, textured or contoured gripping surface, or may be configured for coupling to a robotic arm or other tool (not shown). It is contemplated that such a handle portion may be detachable from the remainder of electrosurgical pencil 120.

Electrosurgical pencil 120 includes a pair of return electrodes 124 that are laterally spaced along the body 121. Return electrodes 124 are coupled to electrosurgical generator 110 through one or more coaxial cables 112. Return electrodes 124 may be placed on opposing surfaces of the body 121 and proximal of the distal tip 128, as shown, or may be placed in any desirable location along the body 121 of electrosurgical pencil 120. Alternatively, a single return electrode 124 may be present, or three or more return electrodes 124 may be placed along the body 121 of electrosurgical pencil 120. Return electrodes 124 may be attached to the body 121 of electrosurgical pencil 120 by stamping, by overmolding, by casting, by overmolding a casting, by coating a casting, by overmolding a stamped electrically conductive plate and/or by overmolding a metal injection molded plate or in other ways customary in the art. Alternatively, electrodes may be placed by inserting hollow tubes of electrically conductive material into the body 121 of electrosurgical pencil 120, or by forming the body 121 of electrosurgical pencil 120 about hollow tubes of electrically conductive material (not shown). Electrodes may additionally be formed of a metal coated with another metal having a higher electrical conductivity, such as copper, silver, or gold.

The body 121 of electrosurgical pencil 120 is formed of a material having a low electrical conductivity and thermal conductivity, and may be formed of a synthetic resin, e.g., an amorphous polyamide such as available from Evonik Industries, under the trademark TROGAMID®, which has an electrical conductivity of $1.0 \cdot e^{-20}$ [S/m] and a thermal conductivity of 0.26 [W/(m·K)]. Other materials having suitable properties of a thermal and electrical insulator are contemplated for the body 121 of electrosurgical pencil 120.

The body 121 of electrosurgical pencil 120 contains an insert 126 formed of a material having a low electrical conductivity and a high thermal conductivity, such as a ceramic material, for example, alumina (aluminum oxide), which has an electrical conductivity of $1.054 \cdot e^{-13}$ [S/m] and a thermal conductivity of 28 [W/(m·K)]. By contrast, human tissue has an electrical conductivity of about 0.512 [W/(m·K)]. Other materials having suitable properties of a thermally conductive electrical insulator are contemplated for insert 126. The surface of insert 126 exposed on the body 121 of electrosurgical pencil 120 is coated with a layer of conductive material 123 (FIG. 3) forming the active electrode 122. Insert 126 and accompanying active electrode 122 may protrude from the body 121 of electrosurgical pencil 120, as shown, or may be flush with body 121.

Figure 2:
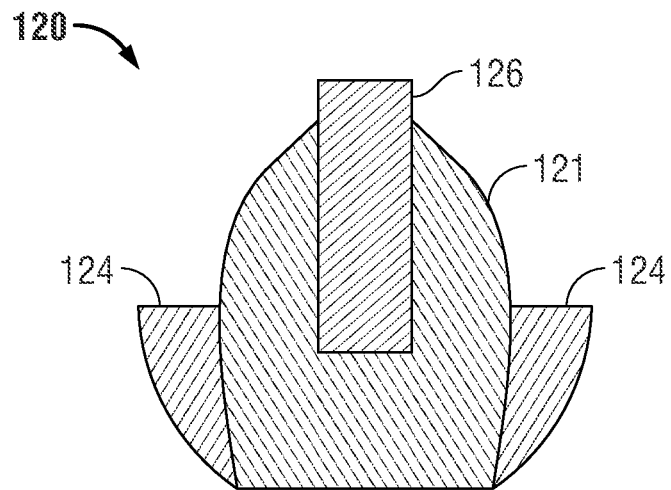
FIG. 2 is a cross-sectional view taken along section line 2-2 of FIG. 1.

Turning to FIG. 2, a cross-sectional view of the electrosurgical pencil 120 taken along section line 2-2 of FIG. 1 is shown. Insert 126 may be disposed along a pre-formed channel within body 121 of electrosurgical pencil 120, or body 121 may be molded around insert 126. Alternatively, insert 126 may be attached to body 121 of electrosurgical pencil 120 by an adhesive, or may have intercooperating surface features with body 121. Additionally, insert 126 may be centered about longitudinal axis A (FIG. 4), or may be offset relative to longitudinal axis A. Insert 126 may be inserted to a partial depth through body 121, or may extend fully therethrough. In such an embodiment, insert 126 would be sandwiched between two portions of body 121 (not shown).

Figure 3:
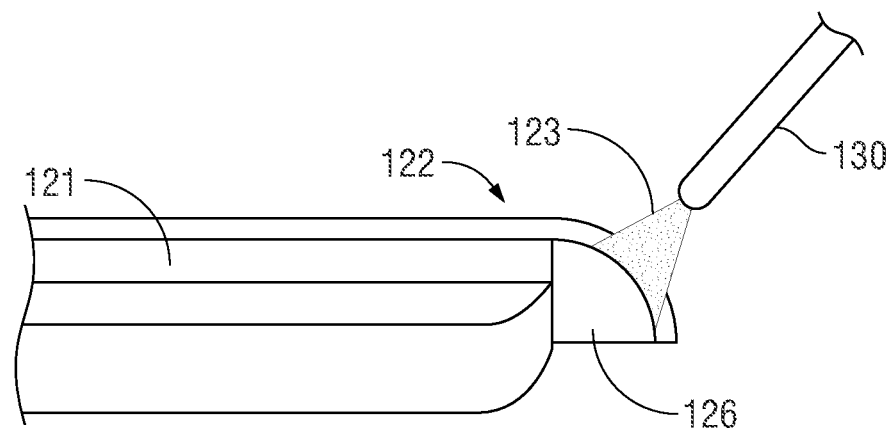
FIG. 3 is an enlarged detail view of the distal tip portion of the electrosurgical pencil of FIG. 1, and showing the formation of an active electrode by a micropen.

Referring to FIG. 3, the formation of active electrode 122 on the body 121 of electrosurgical pencil 120 (FIG. 1) is shown. Active electrode 122 is formed of a layer of conductive material 123 having a high electrical conductivity, such as copper, silver, or gold. Conductive material 123 is deposited along insert 126 electrosurgical pencil 120 with a precision instrument 130 capable of delivering a flow of the conductive material 123, such as a micropen. Precision instrument 130 ensures that the layer of conductive material 123 is deposited in a selected region on insert 126 to ensure that the discharge of RF energy from electrosurgical pencil 120 is concentrated about an area readily manipulated by an operator to dissect desired sections of tissue T (FIG. 4) while leaving other sections of tissue T unaffected.

Turning to FIG. 4, electrosurgical pencil 120 is shown prior to insertion and spaced from a layer of tissue T. RF energy is supplied from electrosurgical generator 110 (FIG. 1) through coaxial cable 112 to active electrode 122 and flows to return electrodes 124. RF energy is transmitted from the return electrodes 124 through the coaxial cable 112 or transmission wires 113 to electrosurgical generator 110, forming a completed circuit. The RF energy is illustrated by current lines "C" is used to dissect tissue T.

Referring to FIGS. 5 and 6, the application of RF energy causes the dissection of tissue T through cutting or ablation such that a path is cleared allowing for advancement of the electrosurgical pencil 120 through tissue T. As described above, the body 121 of electrosurgical pencil 120 may be tapered or blade-like, and may cooperate with electrodes 122, 124 to clear a path through tissue T. Electrosurgical pencil may be inserted to a desired depth "D" in tissue T. The passage of current C from the active electrode 122 to return electrodes 124 also results in the generation of thermal energy "H". Thermal energy H is absorbed and stored by the thermally conductive insert 126. When current C is not passing from active electrode 122 to return electrodes 124 after the electrosurgical generator 110 (FIG. 1) has been shut off or between cycles of AC power supply, thermal energy H is radiated to surrounding tissue T and serves to cauterize tissue T or coagulate blood flowing therefrom. Thus, the passage of current C from the active electrode 122 to return electrodes 124 and the resultant storage and release of thermal energy H from insert 126 serves the purposes of dissecting and otherwise treating tissue T. Accordingly, electrosurgical pencil 120 may be activated and inserted into tissue T to dissect a section of tissue T, while minimizing the loss of fluids such as blood therefrom and maintaining the integrity of the dissected tissue T through cauterization.

Figure 7:
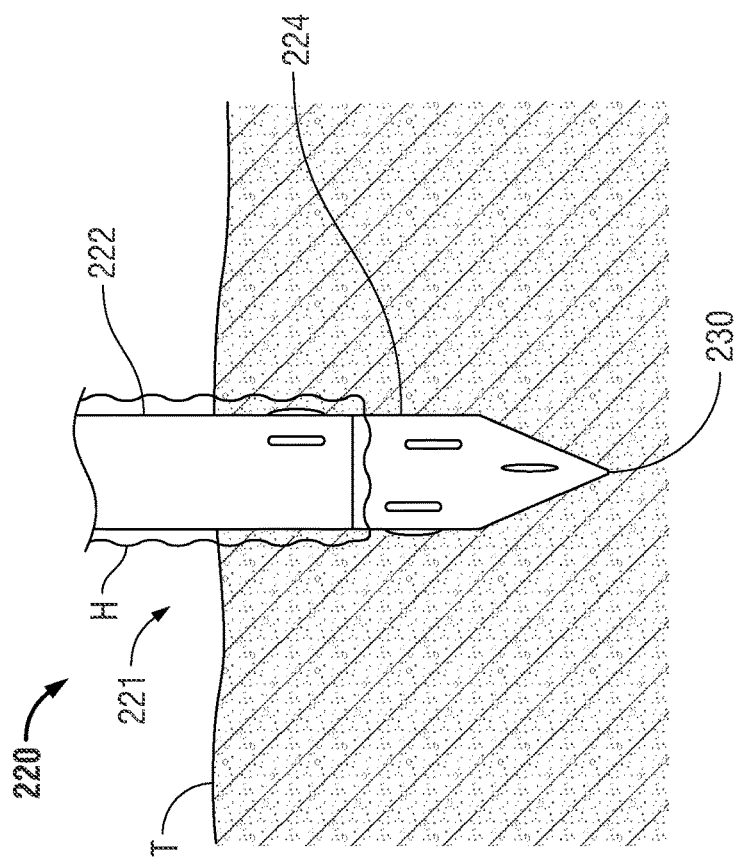
FIG. 7 is a top partial view of an alternate embodiment of an electrosurgical pencil, with electrical current flowing from a plurality of active electrodes to a plurality of return electrodes, and inserted into a layer of tissue.
Figure 8:
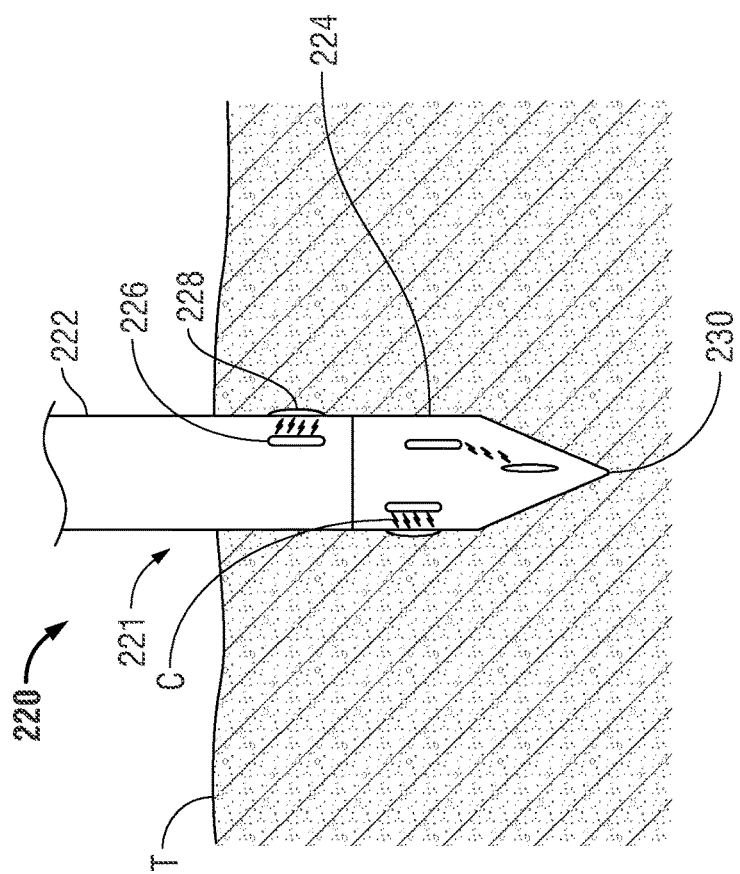
FIG. 8 is a top partial view of the electrosurgical pencil as shown in FIG. 7, with the electrodes inactive and a thermally conductive portion radiating thermal energy to the surrounding tissue.

Turning to FIGS. 7 and 8, an alternate embodiment of the presently disclosed electrosurgical pencil, designated 220, is shown. Electrosurgical pencil 220 is configured to be electrically coupled to an electrosurgical generator 110 (FIG. 1) through coaxial cable 112 and transmission wires 113 (FIG. 1) as with electrosurgical pencil 120 described above. Electrosurgical pencil 220 has a body 221 that includes a proximal section 222 formed of a thermal conductor such as alumina, and a distal section 224 formed of a thermal insulator made from a synthetic resin, e.g., an amorphous polyamide such as available from Evonik Industries, under the trademark TROGAMID®. Other materials having suitable thermal properties are contemplated for proximal and distal sections 222, 224 of body 221. Body 221 of electrosurgical pencil 220 may be tapered or otherwise configured, and may have a distal tip that is sharpened, rounded, or blunt.

Active electrodes 226 and return electrodes 228 are disposed on the body 221 of electrosurgical pencil 220. Active electrodes 226 and return electrodes 228 are formed in a substantially similar manner as the active electrodes 122 and return electrodes 124 of FIG. 1 and may be placed in any desirable pattern along body 221 of electrosurgical pencil 220 such that the distribution of current C is optimized for incision into tissue T.

The thermal profile of electrosurgical pencil 220 differs from that of electrosurgical pencil 120 described above, in that thermal energy H is stored within the proximal section 222 of body 221. When current C is not flowing between active and return electrodes 226, 228, thermal energy H is released from the proximal section 222 of body 221 into surrounding tissue T to treat tissue T through cauterization and to coagulate blood flowing therefrom. Thus, electrosurgical pencil 220 provides for dissection of tissue T through the use of RF energy, and proximal section 222 of body 221 is configured to store and release thermal energy H in a manner such that tissue T is cauterized and blood is coagulated in the wake of the advancement of distal tip 230. Electrosurgical pencil 220 allows for initial tissue penetration by the current C flowing from active electrodes 226 to return electrodes 228, and the thermal profile of body 221 facilitates the smooth advancement of electrosurgical pencil 220 through tissue T by the release of thermal energy H from proximal section 222 of body 221.

Figure 9:
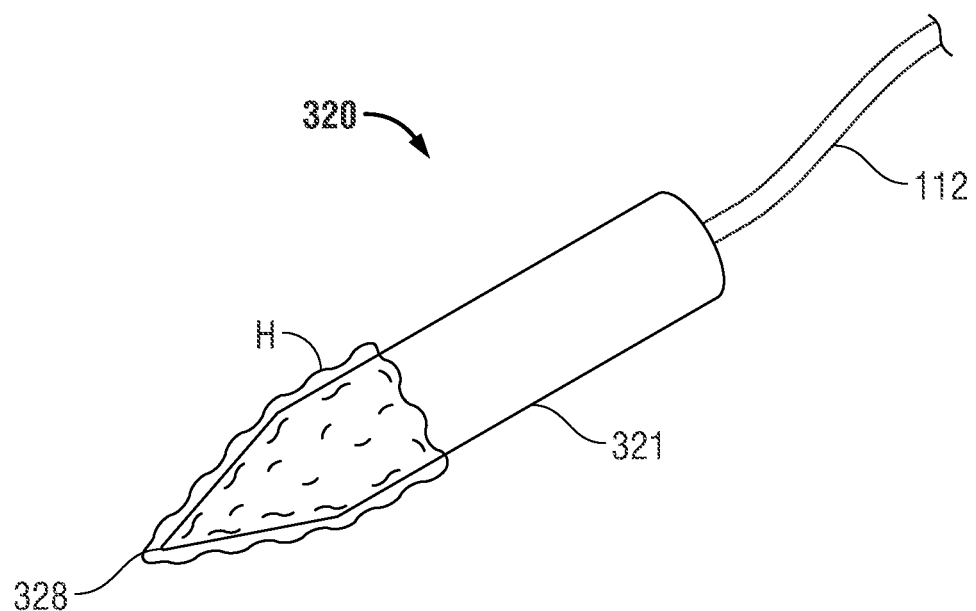
FIG. 9 is a perspective view of an alternate embodiment of an electrosurgical pencil having a tapered body and corresponding thermal profile.

Turning to FIG. 9, an alternate embodiment of the presently disclosed electrosurgical pencil, designated 320, is shown. Electrosurgical pencil 320 is configured to be electrically coupled to an electrosurgical generator 110 (FIG. 1) through coaxial cable 112 and transmission wires 113 (FIG. 1) as with electrosurgical pencil 120 (FIG. 1) described above. Electrosurgical pencil 320 has a tapered elongate body 321 that converges toward a distal tip 328. Body 321 of electrosurgical pencil 320 may be formed of a thermally conductive material such as stainless steel, though electrosurgical pencil 320 may be formed of other materials.

During the flow of current from active electrodes to return electrodes as described in the previous embodiments, thermal energy is generated and stored in the body 321 of electrosurgical pencil 320. As the diameter of the body 321 of electrosurgical pencil 320 increases from a distal end toward the proximal tip 328, more mass is available for thermal energy storage towards the proximal end of the body 321. Accordingly, the thermal profile of electrosurgical pencil 320 is such that more thermal energy "H" is stored and released toward the proximal end of the body 321. Thus, electrosurgical pencil 320 is configured to store and release thermal energy H in a manner such that tissue T (FIG. 4) is cauterized and blood is coagulated in the wake of the advancement of distal tip 328. Electrosurgical pencil 320 allows for initial tissue penetration by current flowing from active electrodes to return electrodes, as described in the previous embodiments, and the thermal profile of body 321 facilitates the smooth advancement of electrosurgical pencil 320 through tissue by the increased release of thermal energy H from a proximal section of body 321.

Figure 10:
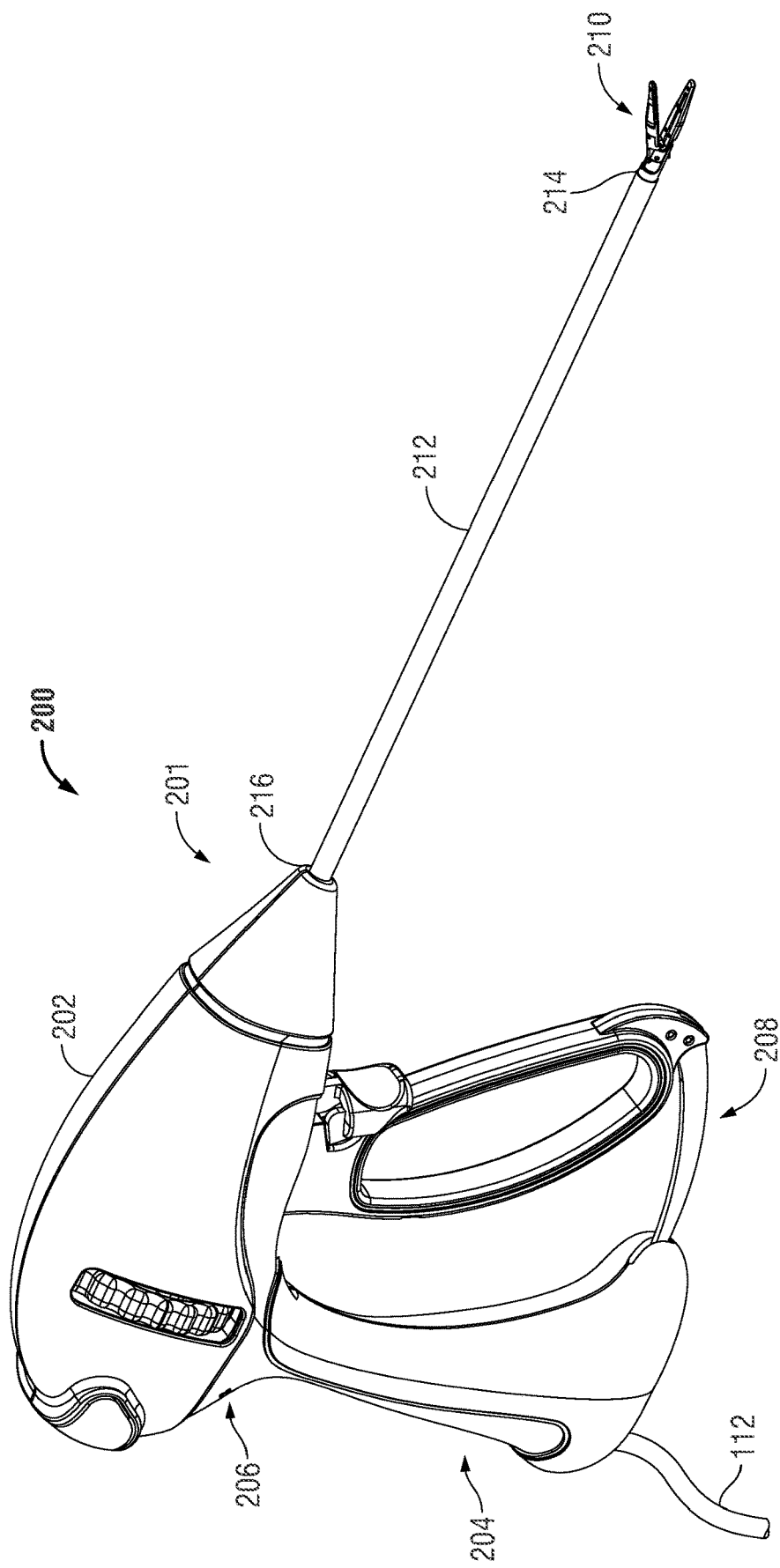
FIG. 10 is a perspective view of an electrosurgical apparatus according to the present disclosure.

Turning now to FIG. 10, another embodiment of the present disclosure is shown. Electrosurgical system 200 includes an electrosurgical generator (not shown) such as electrosurgical generator 110 (FIG. 1), and an electrosurgical dissection apparatus such as electrosurgical forceps 201 for treating tissue. RF energy is supplied from electrosurgical generator 110 (FIG. 1) to forceps 201 through coaxial cable 112.

The forceps 201 is configured to support an effector assembly 210 and generally includes a housing 202, a handle assembly 204, a rotating assembly 206, and a trigger assembly 208 that mutually cooperate with the end effector assembly 210 to grasp, seal and, if required, divide tissue. Electrosurgical forceps 201 also includes a shaft 212 that has a distal end 214 that mechanically engages the end effector assembly 210 and a proximal end 216 that mechanically engages and is retained by the housing 202.

Figure 11:
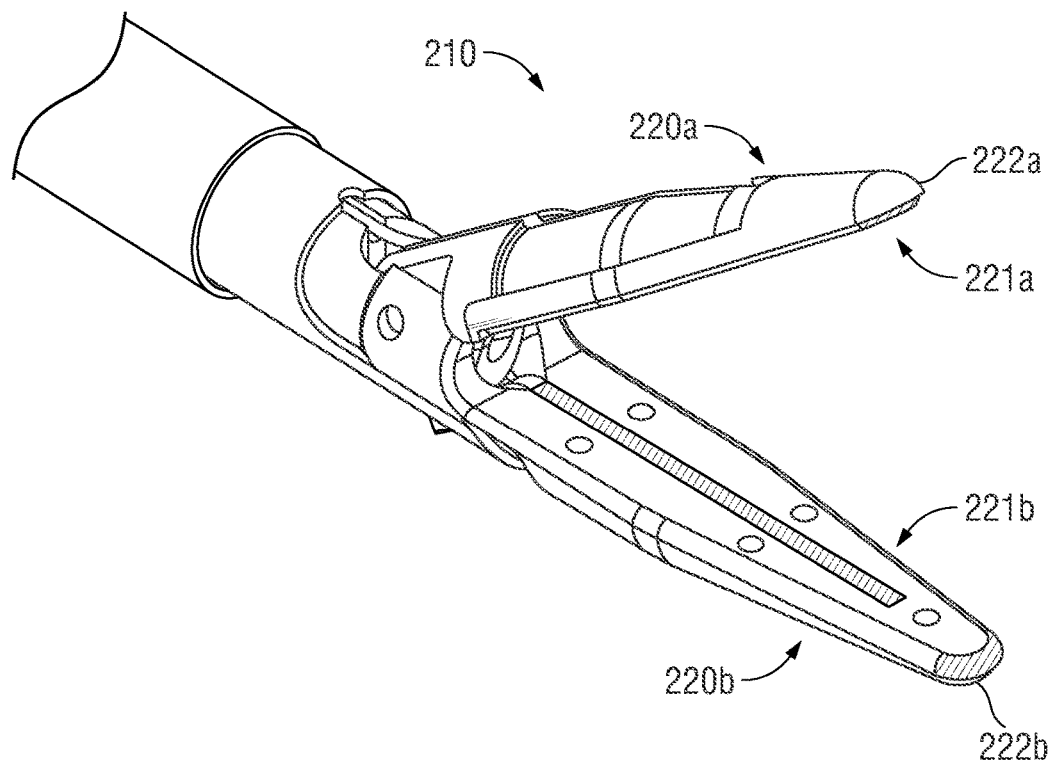
FIG. 11 is a perspective detail of the jaw members of the electrosurgical apparatus of FIG. 10.
Figure 12:
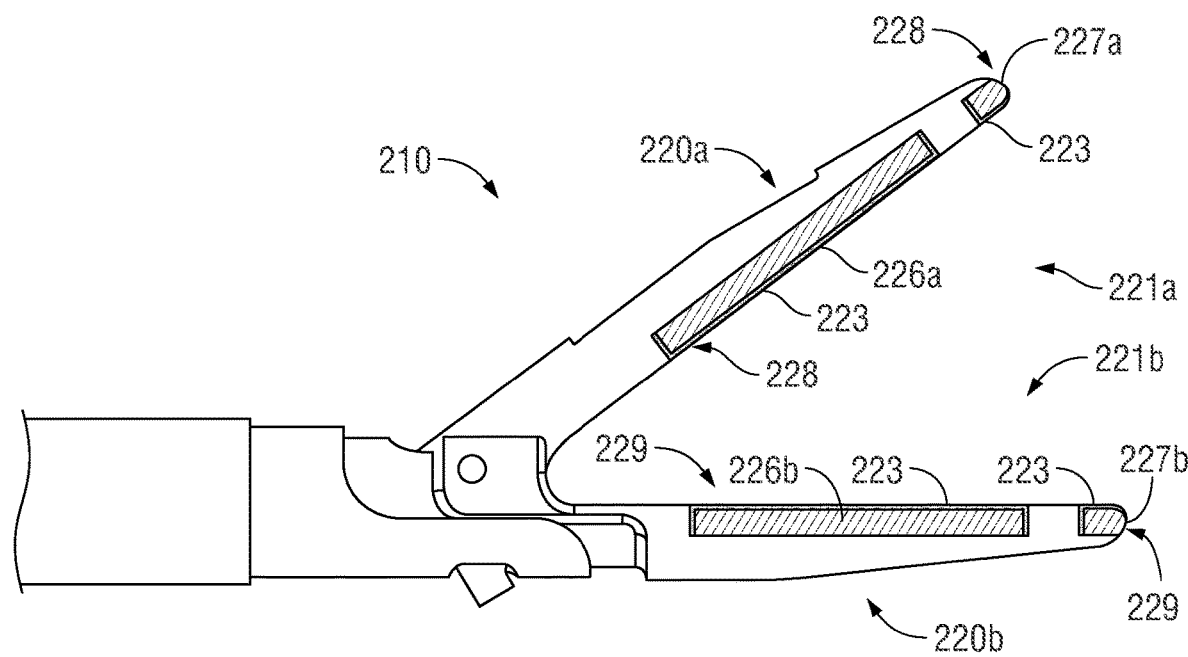
FIG. 12 is a side detail, shown in cutaway, of the jaw members of the electrosurgical apparatus of FIG. 10.

Referring to FIGS. 11 and 12, end effector assembly 210 includes a pair of opposing jaw members 220a, 220b each having an electrically conductive sealing plate 221a, 221b, respectively, attached thereto for conducting electrosurgical energy through tissue "T" (FIG. 13) held therebetween. More particularly, the jaw members 220a, 220b are configured for relative approximation and move from an open position to a closed position in response to actuation of handle assembly 204 (FIG. 10). In the open position, the sealing plates 221a, 221b are disposed in spaced relation relative to one another. In a clamping or closed position, the sealing plates 221a, 221b cooperate to grasp tissue T and apply electrosurgical energy thereto.

Jaw members 220a, 220b are activated using a drive assembly (not shown) enclosed within the housing 202 (FIG. 10). The drive assembly cooperates with the handle assembly 204 to impart movement of the jaw members 220a, 220b from the open position to the clamping or closed position. Examples of handle assemblies are shown and described in commonly-owned U.S. Pat. No. 7,156,846 entitled "VESSEL SEALER AND DIVIDER FOR USE WITH SMALL TROCARS AND CANNULAS" the entire contents of which are hereby incorporated by reference herein in its entirety.

Sealing plates 221a, 221b of jaw members 220a, 220b are formed of a synthetic resin material having a low electrical conductivity and thermal conductivity, e.g., a amorphous polyamide such as available from Evonik Industries, under the trademark TROGAMID®', which has an electrical conductivity of $1.0 \cdot e^{-20}$ [S/m] and a thermal conductivity of 0.26 [W/(m·K)]. Other materials having suitable properties of a thermal and electrical insulator are contemplated for the sealing plates 221a, 221b of jaw members 220a, 220b. In embodiments, other portions or the entirety of jaw members 220a, 220b may be formed of such materials.

Jaw members 220a, 220b contain at least one insert 226a, 226b formed of a material having a low electrical conductivity and a high thermal conductivity, such as a ceramic material, for example, alumina (aluminum oxide), which has an electrical conductivity of $1.054 \cdot e^{-13}$ [S/m] and a thermal conductivity of 28 [W/(m·K)]. By contrast, human tissue has an electrical conductivity of about 0.512 [W/(m·K)]. Other materials having suitable properties of a thermally conductive electrical insulator are contemplated for inserts 226a, 226b. Inserts 226a, 226b may be configured as an elongated strip of material. The surface of inserts 226a, 226b is exposed on the respective sealing plate 221a, 221b of each jaw member 220a, 220b. Inserts 226a, 226b may be disposed along a pre-formed channel within each jaw member 220a, 220b, or each jaw member 220a, 220b may be molded around respective inserts 226a, 226b. Alternatively, inserts 226a, 226b may be attached to each jaw member 220a, 220b by an adhesive, or may have intercooperating surface features with each jaw member 220a, 220b. Inserts 226a, 226b may be inserted to a partial depth through each jaw member 220a, 220b, or may extend fully therethrough. In such an embodiment, inserts 226a, 226b would be sandwiched between adjacent portions of each jaw member 220a, 220b (not shown).

Inserts 226a, 226b are coated with a layer of conductive material 223, forming an active electrode 228 or a return electrode 229. Active electrode 228 is disposed opposite return electrode 229 to effect bipolar RF transmission, as will be described further below. Inserts 226a, 226b and the associated conductive material 223 may protrude from the sealing plates 221a, 221b of jaw members 220a, 220b, as shown, or may be flush with jaw members 220a, 220b.

An additional insert 227a, 227b may be disposed on a front face 222a, 222b of each respective jaw member 220a, 220b, as shown, and may be configured as a strip of alumina or another similar material as described above. Inserts 227a, 227b may be coated with a layer of conductive material 223 as described above, and may be configured to operate as the active electrode 228 or the return electrode 229.

Figure 13:
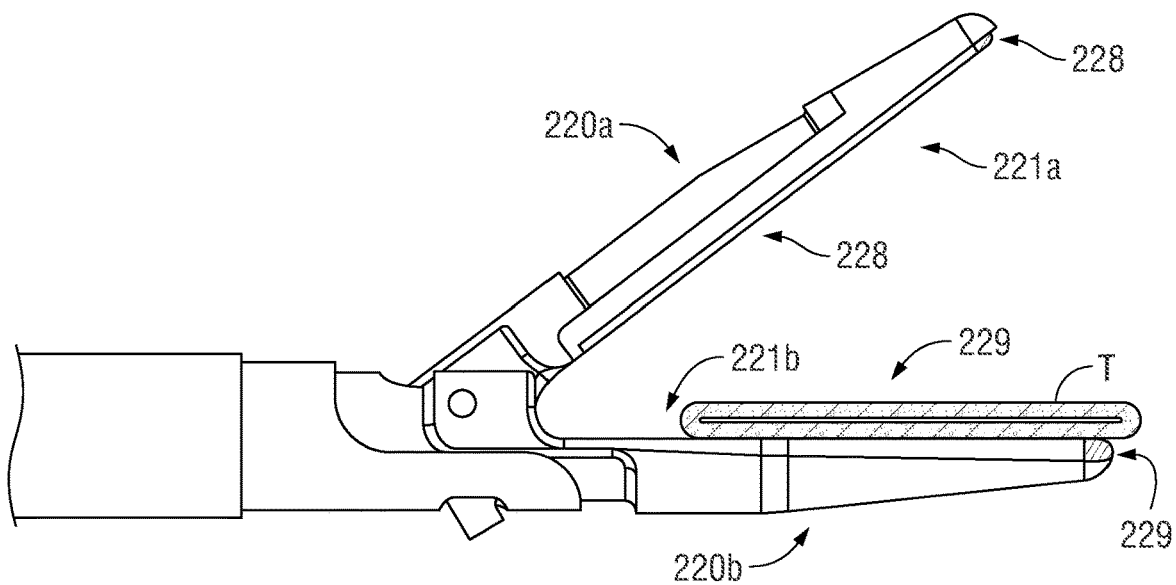
FIG. 13 is a side detail of the jaw members of the electrosurgical apparatus of FIG. 10 spaced apart about a layer of tissue.
Figure 14:
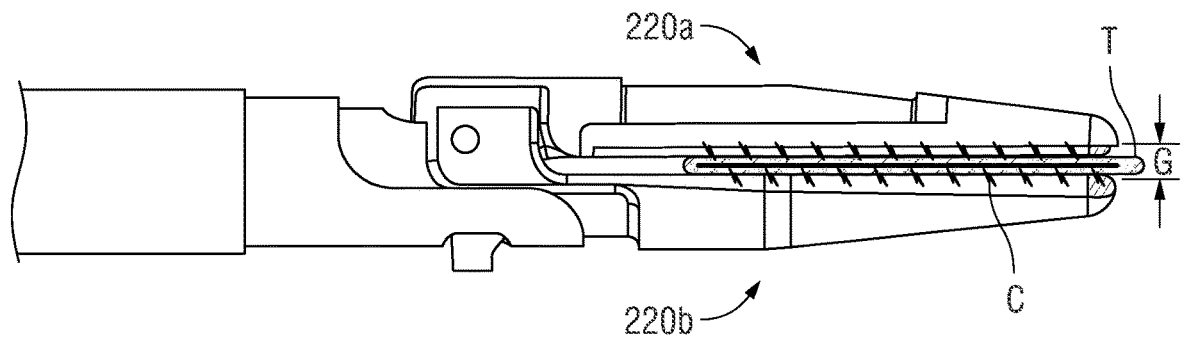
FIG. 14 is a side detail of the jaw members of the electrosurgical apparatus of FIG. 10 clamping a layer of tissue and transmitting current therethrough.
Figure 15:
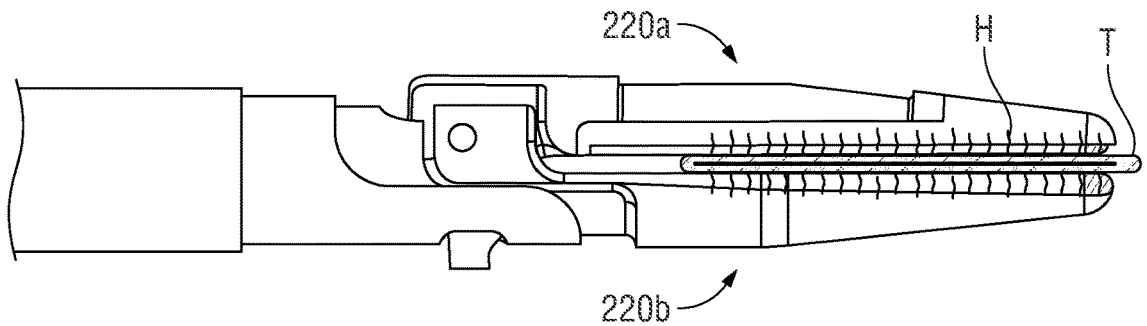
FIG. 15 is a side detail of the jaw members of the electrosurgical apparatus of FIG. 10 clamping a layer of tissue and radiating heat therethrough.

Referring to FIGS. 13-15, the application of RF energy causes the sealing of tissue T. As noted above, jaw members 220a, 220b may be approximated to a closed configuration to clamp tissue T. It should be noted that two mechanical factors play an important role in determining the resulting thickness of the sealed tissue T and the effectiveness of the seal, i.e., the pressure applied between the opposing jaw members 220a, 220b (between about 3 kg/cm² to about 16 kg/cm²) and the gap distance "G" between the opposing sealing plates 221a, 221b of the jaw members 220a, 220b, respectively, during the sealing process (between about 0.001 inches to about 0.006 inches). One or more stop members (not shown) may be employed on one or both sealing plates 221a, 221b to control the gap distance. A third mechanical factor has recently been determined to contribute to the quality and consistency of a tissue seal, namely, the closure rate of the electrically conductive surfaces or sealing plates 221a, 221b during electrical activation.

The passage of current C between the active electrodes 228 and return electrodes 229 also results in the generation of thermal energy "H". Thermal energy H is absorbed and stored by the thermally conductive inserts 226a, 226b, 227a, 227b (FIG. 12). When current C is not passing between the active electrodes 228 and return electrodes 229 after the electrosurgical generator 110 (FIG. 1) has been shut off or between cycles of AC power supply, thermal energy H is radiated to surrounding tissue T and serves to cauterize tissue T or coagulate blood flowing therefrom. Thus, the passage of current C between the active electrodes 228 and return electrodes 229 and the resultant storage and release of thermal energy H from inserts 226, 227 serves the purposes of sealing or otherwise treating tissue T. Accordingly, electrosurgical forceps 201 may be activated and inserted into tissue T to seal a section of tissue T, while minimizing the loss of fluids such as blood therefrom and maintaining the integrity of the dissected tissue T through cauterization.

While several aspects of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular aspects. Those skilled in the art will envision other modifications within the scope and spirit of the claims appended hereto.

What is claimed is:

1. An electrosurgical pencil comprising:
   a proximal portion formed of a thermal conductor including:
      a first active electrode disposed on the thermal conductor, and
      a first return electrode disposed on the thermal conductor; and
   a distal portion formed of a thermal insulator including:
      a second active electrode, different from the first active electrode, disposed on the thermal insulator, and
      a second return electrode, different from the first return electrode, disposed on the thermal insulator,
   wherein the thermal conductor is configured to store thermal energy when radiofrequency energy is passing from the first active electrode to the first return electrode and cauterize tissue by releasing the stored thermal energy when radiofrequency energy is not passing from the first active electrode to the first return electrode.

2. The electrosurgical pencil of claim 1, wherein the distal portion includes a distal tip, wherein a shape of the distal tip is one of sharpened, rounded, or blunt.

3. The electrosurgical pencil of claim 1, wherein the first active electrode is formed of one of copper, silver, or gold.

4. The electrosurgical pencil of claim 1, wherein the thermal insulator is formed from an amorphous polyamide.

5. The electrosurgical pencil of claim 1, wherein the thermal conductor is formed from alumina.

6. The electrosurgical pencil of claim 5, wherein the first active electrode is formed from one of copper, silver, or gold.

7. The electrosurgical pencil of claim 1, wherein the first active electrode is formed from a coating of conductive material.

8. An electrosurgical dissection system comprising:
   an electrosurgical generator configured to generate electrosurgical energy;
   an electrosurgical pencil comprising:
      a proximal portion formed of a thermal conductor including:
         a first active electrode disposed on the thermal conductor, and
         a first return electrode disposed on the thermal conductor;
      a distal portion formed of a thermal insulator including:
         a second active electrode, different from the first active electrode, disposed on the thermal insulator, and
         a second return electrode, different from the first return electrode, disposed on the thermal insulator,
      wherein the thermal conductor is configured to store thermal energy when radiofrequency energy is passing from the first active electrode to the first return electrode and to cauterize tissue by releasing the stored thermal energy when radiofrequency energy is not passing from the first active electrode to the first return electrode; and
   a cable connecting the electrosurgical generator to the electrosurgical pencil.

9. The electrosurgical system of claim 8, wherein the distal portion of the electrosurgical pencil includes a distal tip, wherein a shape of the distal tip is one of sharpened, rounded, or blunt.

10. The electrosurgical dissection system of claim 9, wherein the first active electrode is formed from a coating of conductive material.

11. The electrosurgical dissection system of claim 10 wherein the first active electrode is formed from one of copper, silver, or gold.

12. The electrosurgical dissection system of claim 8, wherein the first active electrode is formed of one of copper, silver, or gold.

13. The electrosurgical dissection system of claim 8, wherein the thermal insulator is formed from an amorphous polyamide.

14. The electrosurgical dissection system of claim 8, wherein the thermal conductor is formed from alumina.

* * * * *